(12) United States Patent
Takano et al.

(10) Patent No.: US 8,178,731 B2
(45) Date of Patent: May 15, 2012

(54) PROCESS FOR PRODUCING TRIPHENYLENE COMPOUND AND CRYSTAL OBTAINED BY THE PROCESS

(75) Inventors: Daisuke Takano, Kawagoe (JP); Tomokazu Kato, Kawagoe (JP); Toshihiro Fujinaka, Kawagoe (JP); Kazunori Sakamoto, Kawagoe (JP)

(73) Assignee: Wako Pure Chemical Industries, Ltd., Osaka (JP)

( * ) Notice: Subject to any disclaimer, the term of this patent is extended or adjusted under 35 U.S.C. 154(b) by 0 days.

(21) Appl. No.: 13/044,975

(22) Filed: Mar. 10, 2011

(65) Prior Publication Data

US 2011/0201845 A1    Aug. 18, 2011

Related U.S. Application Data

(63) Continuation of application No. 12/670,707, filed as application No. PCT/JP2008/064163 on Aug. 6, 2008, now Pat. No. 7,964,757.

(30) Foreign Application Priority Data

Aug. 7, 2007  (JP) .................................. 2007-205874

(51) Int. Cl.
C07C 39/12     (2006.01)
C07C 39/14     (2006.01)
(52) U.S. Cl. ...................................................... 568/719
(58) Field of Classification Search ............... 568/719
See application file for complete search history.

(56) References Cited

FOREIGN PATENT DOCUMENTS

| JP | 7-330650 A | 12/1995 |
|---|---|---|
| JP | 8-119894 A | 5/1996 |
| JP | 9-118642 A | 5/1997 |
| JP | 2005-104870 A | 4/2005 |
| JP | 2005-225812 A | 8/2005 |
| WO | WO 2005/090275 A1 | 9/2005 |

OTHER PUBLICATIONS

International Search Report of PCT/JP2008/064163, dated Sep. 9, 2008.

Naarmann et al. "A High Yield Easy Method for the Preparation of Alkoxy-Substituted Triphenylenes." Synthesis, May 1994, pp. 477-478.

Beattie et al. "Triphenylene Hexa-n-alkylcyclohexanoates: a New Series of Disc-like Liquid Crystals." J. Mater Chem, 2(12), 1992, pp. 1261-1266.

*Primary Examiner* — Sikarl Witherspoon
(74) *Attorney, Agent, or Firm* — Hamre, Schumann, Mueller & Larson, P.C.

(57) ABSTRACT

An object of the present invention is to provide a process for producing high-purity hydroxytriphenylenes in which not only inexpensive raw materials can be used but also no complicated steps of deprotection such as dealkylation, and reduction and the like are necessary, and which is thereby advantageous in industrial production. Also there is provided a novel crystal of 2,3,6,7,10,11-hexahydroxytriphenylene monohydrate, which has satisfactory thermal stability. The process for producing a compound represented by the general formula (2) is characterized by reacting a compound represented by the general formula (1) in the presence of a metal oxide comprising a metal selected from trivalent iron, pentavalent vanadium and hexavalent molybdenum and of a nonvolatile strong acid:

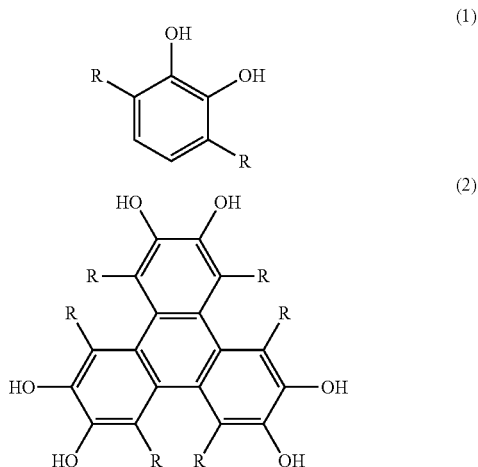

wherein, Rs are each independently a hydrogen atom, a halogen atom, an alkyl group having 1 to 3 carbon atoms or an alkoxy group having 1 to 3 carbon atoms.

3 Claims, 5 Drawing Sheets

PROCESS FOR PRODUCING TRIPHENYLENE COMPOUND AND CRYSTAL OBTAINED BY THE PROCESS

TECHNICAL FIELD

The present invention relates to a process for producing hydroxytriphenylenes which are useful as a raw material for functional materials such as, for example, discotic liquid crystal, in more detail, the present invention relates to a process for producing hydroxytriphenylenes in which 1,2-dihydroxybenzenes (hereinafter, may be referred to simply as catechols) is used as a raw material, and a crystal obtained by the process, as well as a novel crystal of 2,3,6,7,10,11-hexahydroxytriphenylene monohydrate.

BACKGROUND OF THE INVENTION

Discotic liquid crystal has generally a disc-like central mother nucleus and side chains extending radially from the mother nucleus thereof, and recently various studies have been done in the liquid crystal field due to anomalous liquid crystal property coming from its structure. Examples of a compound to be the central mother nucleus of the discotic liquid crystal are exemplified by, for example, benzene derivatives, truxene derivatives, phthalocyanine derivatives, triphenylene derivatives, cyclohexane derivatives, porphyrin derivatives, and the like, and among them, triphenylene derivatives are the compounds which attract attention in recent year because they tend to form a discotic nematic phase, which is effective to form an optical functional device.

Among these triphenylene derivatives, particularly various production processes for 2,3,6,7,10,11-hexahydroxytriphenylene have been reported since before, because suitable side chains can be easily introduced at the positions of six hydroxyl groups and the other reason etc.

Specifically, processes for producing a desired 2,3,6,7,10,11-hexahydroxytriphenylene have been known, by synthesizing firstly chemically stable 2,3,6,7,10,11-hexaalkoxytriphenylene with using 1,2-dialkoxybenzene as a raw material (see, JP-A-7-330650, Synthesis, 477, 1994, etc.), then dealkylating with boron tribromide, hydrogen iodide, and the like (see, JP-A-8-119894, J. Mater. Chem., 1992, 2, 1261, etc.). However, since these processes not only required two steps of trimerization step and dealkylation step, but also had such problems that 1,2-dialkoxybenzene as a raw material was comparatively expensive, and boron tribromide and hydrogen iodide to be used in the dealkylation step were highly corrosive, and the like, these processes were not suitable as an industrial process for producing 2,3,6,7,10,11-hexahydroxytriphenylene.

As a method to solve such problems, a process for producing directly 2,3,6,7,10,11-hexahydroxytriphenylene with using 1,2-dihydroxybenzene as a raw material has been attempted (see, JP-A-9-118642, Synthesis, 477, 1994, etc.). Specifically, in Synthesis, 477, 1994, an iron complex of 2,3,6,7,10,11-hexahydroxytriphenylene has been obtained by reacting catechol in the presence of anhydrous ferric (III) chloride and 9.5-fold moles or more of sulfuric acid. However, it has not been described that 2,3,6,7,10,11-hexahydroxytriphenylene has been isolated from the iron complex. In addition, in JP-A-9-118642, desired 2,3,6,7,10,11-hexahydroxytriphenylene has been obtained by reacting catechol in the presence of ferric (III) chloride hydrate to obtain an iron complex and/or a quinone derivative of 2,3,6,7,10,11-hexahydroxytriphenylene, which been then subjected to reduction treatment. Thus, in these processes, although the problems of productivity and corrosion can be solved because dealkylation step is not required by using catechol as a raw material, the problem of requiring many steps has not been solved because a reduction step is necessary to obtain high-purity 2,3,6,7,10,11-hexahydroxytriphenylene in addition to a trimerization step of catechol. Thus, these processes were not advantageous one as an industrial production process.

Under such circumstance, a development of a production process for synthesizing a high-purity 2,3,6,7,10,11-hexahydroxytriphenylene has been demanded, in which not only inexpensive raw materials can be used but also complicated steps of deprotection such as dealkylation from alkoxy groups in hexaalkoxytriphenylene, and reduction of an iron complex and/or a quinone derivative of hexahydroxytriphenylene are not necessary, and which is thereby more easy and simple.

In addition, recently, as a technology relating to a crystal form of 2,3,6,7,10,11-hexahydroxytriphenylene monohydrate, type A crystal of the monohydrate has been disclosed in WO2005/090275. It has been described that the type A crystal can be obtained by distilling off acetone from a solution of 2,3,6,7,10,11-hexahydroxytriphenylene in mixed solvent of acetone-water under a reduced pressure and a specified temperature condition, and that the crystal form is superior in thermal stability with a thermal decomposition temperature (Td) at about 139° C. In addition, in the WO2005/090275, it has been described that all crystals (type B crystal in WO2005/090275) of 2,3,6,7,10,11-hexahydroxytriphenylene obtained by the well-known production process in the prior art are poor in thermal stability, and that an equipment built-in with the type B crystal is poor in durability and has a disadvantage that it cannot exhibit a desired performance over a long period of time. As obvious from this, the type B crystal obtained by the existing production process did not have satisfactory performance.

Under such circumstance, an improvement from type B crystal of 2,3,6,7,10,11-hexahydroxytriphenylene monohydrate having a poor thermal stability to the one having a thermal stability comparable to at least that of type A crystal of the monohydrate, that is, 2,3,6,7,10,11-hexahydroxytriphenylene monohydrate having a superior thermal stability as well as an establishment of a production process for the compound has been demanded.

DISCLOSURE OF INVENTION

Problem to be Solved by the Invention

The present invention has been made considering the aforementioned circumstances, and is directed to provide a process for producing high-purity hydroxytriphenylenes in which not only inexpensive raw materials can be used but also complicated steps of deprotection such as dealkylation, and reduction and the like are not necessary, and which is thereby advantageous in industrial production, and further a process for producing a crystal of the hydroxyltriphenylenes.

In addition, the present invention is directed to provide novel two types of crystals (hereinafter, may be referred to as type B' crystal and type C crystal) of 2,3,6,7,10,11-hexahydroxytriphenylene monohydrate having a superior thermal stability, which can be obtained by the aforementioned production process.

Means to Solving the Problem

The present invention is an invention of a process for producing a compound represented by the general formula (2) which comprises reacting a compound represented by the general formula (1) in the presence of a metal oxide comprising a metal selected from trivalent iron, pentavalent vanadium and hexavalent molybdenum, and of a nonvolatile strong acid:

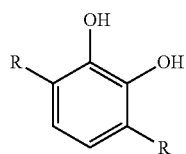
(1)

wherein, two Rs are each independently a hydrogen atom, a halogen atom, an alkyl group having 1 to 3 carbon atoms or an alkoxy group having 1 to 3 carbon atoms,

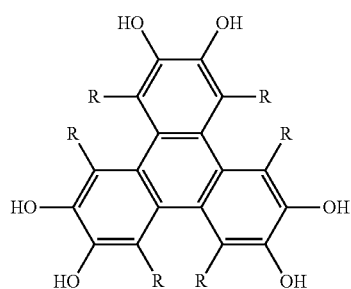
(2)

wherein, six Rs are same as mentioned above.

In addition, the present invention is an invention of a crystal of 2,3,6,7,10,11-hexahydroxytriphenylene monohydrate obtained by reacting catechol in the presence of a metal oxide comprising a metal selected from trivalent iron, pentavalent vanadium and hexavalent molybdenum and of a nonvolatile strong acid, dissolving the resultant 2,3,6,7,10,11-hexahydroxytriphenylene in a mixed solvent of acetone and water, and then distilling off acetone from a obtained solution at a temperature in a range from 56 to 95° C.

Further, the present invention is an invention of a crystal of 2,3,6,7,10,11-hexahydroxytriphenylene monohydrate obtained by reacting catechol in the presence of a metal oxide comprising a metal selected from trivalent iron, pentavalent vanadium and hexavalent molybdenum and of a nonvolatile strong acid, dissolving the resultant 2,3,6,7,10,11-hexahydroxytriphenylene in a mixed solvent of acetone and water, and then adding water to a obtained solution at a temperature in a range from 5 to 50° C.

Furthermore, the present invention is an invention of a crystal of 2,3,6,7,10,11-hexahydroxytriphenylene monohydrate having, in a X-ray diffraction spectrum for CuKα characteristic X-ray (wavelength: 1.5418 Å), main peaks at 9.3, 10.2 and 26.4 in Bragg angle (2θ±0.2°) thereof, and not having any peak between 10.5 and 12.5.

Effect of the Invention

According to the production process of the present invention, the process not only has high productivity because a compound represented by the general formula (1) (catechols) is used as a raw material, but also can be synthesized in one step requiring no complicated step of deprotection such as dealkylation, and reduction, and the like, and further has less environmental load because oxidizing agent such as organic peroxides is not used. Thus, high-purity 2,3,6,7,10,11-hexahydroxytriphenylenes can be produced more easily and more simply.

In addition, since two types of crystals of 2,3,6,7,10,11-hexahydroxytriphenylene monohydrate of the present invention obtained by recrystallizing 2,3,6,7,10,11-hexahydroxytriphenylene produced by the above process with using catechol as a raw material under a specified condition, that is, type B' crystal and type C crystal, have more superior thermal stability in comparison with type B crystal obtained by the existing process, an equipment built-in with the crystal of the present invention as a raw material of a functional material has a superior stability (resistance to denaturalization) and can exhibit a desired performance over a long period of time.

BEST MODES FOR CARRYING-OUT OF THE INVENTION

Figure 1:
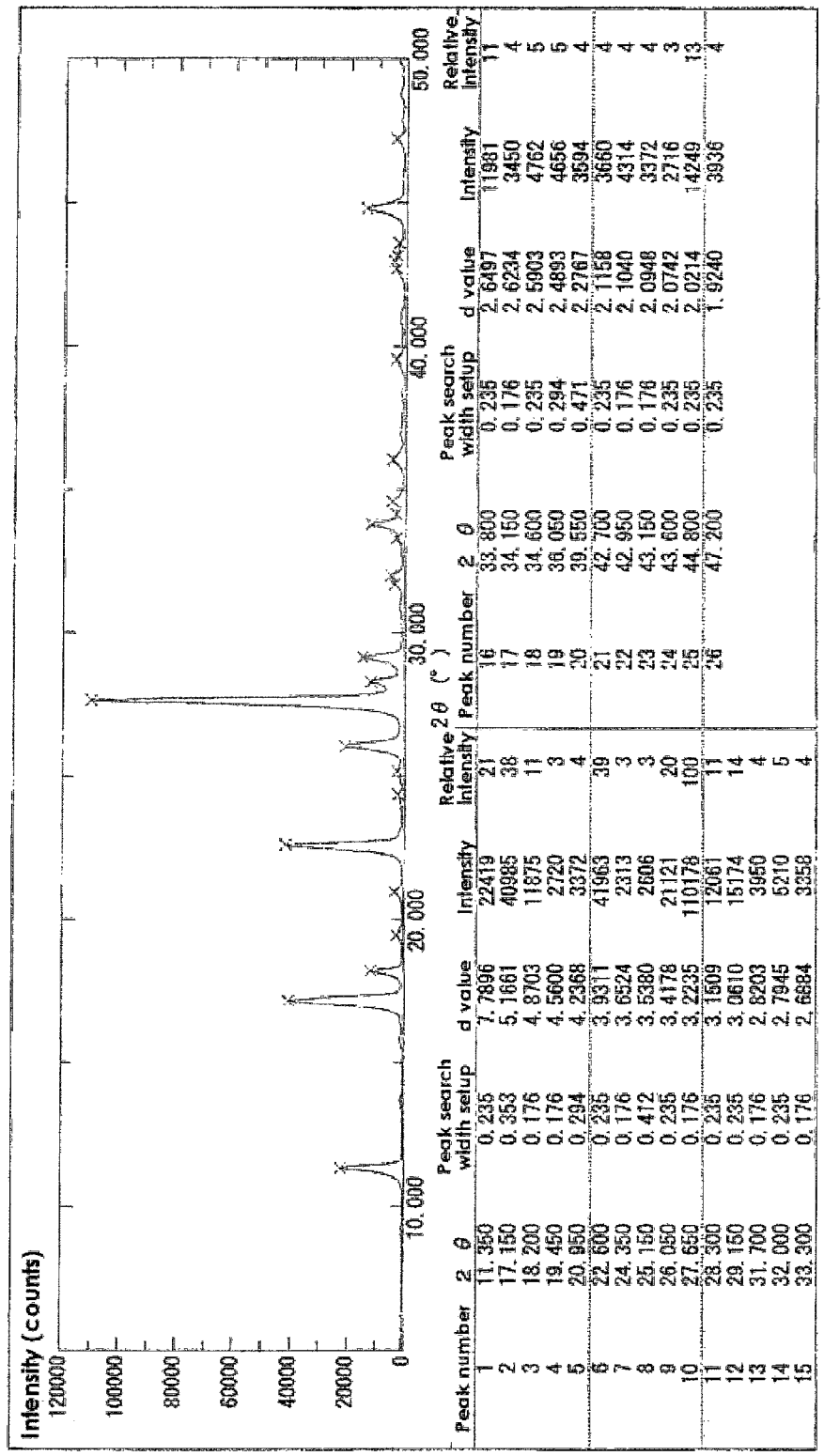
FIG. 1 is a figure showing an X-ray diffraction spectrum of type B' crystal of 2,3,6,7,10,11-hexahydroxytriphenylene monohydrate obtained in Example 4.

The halogen atom represented by R in the general formulae (1) and (2) includes a fluorine atom, a chlorine atom, a bromine atom, an iodine atom, and the like. Among them, a fluorine atom, a chlorine atom and a bromine atom are preferable, and a chlorine atom and a bromine atom are more preferable.

The alkyl group having 1 to 3 carbon atoms represented by R in the general formulae (1) and (2) may be any type of straight-chained or branched, and specifically includes, for example, a methyl group, an ethyl group, a n-propyl group, an isopropyl group, and the like. Among them, a methyl group and an ethyl group are preferable, and a methyl group is more preferable.

The alkoxy group having 1 to 3 carbon atoms represented by R in the general formulae (1) and (2) may be any type of straight-chained or branched, and specifically includes, for example, a methoxy group, an ethoxy group, a n-propoxy group, an isopropoxy group, and the like. Among them, a methoxy group and an ethoxy group are preferable, and a methoxy group is more preferable.

As R in the general formulae (1) and (2), a hydrogen atom is more preferable.

In the production process of the present invention, the compound represented by the general formula (2) can be synthesized by trimerizing the compound represented by the general formula (1) in water and/or a polar solvent, in the presence of a specified amount of a metal oxide comprising a metal selected from trivalent iron, pentavalent vanadium and hexavalent molybdenum, relative to the compound represented by the general formula (1), and of a nonvolatile strong acid. Further, two types of crystals of monohydrate of the compound represented by the general formula (2) can be selectively produced by selecting post-treatment procedures mentioned later, so-called isolation and purification procedures for the reaction solution after the trimerization reaction. In addition, both of the two types of crystals (type B' crystal and type C crystal) of 2,3,6,7,10,11-hexahydroxytriphenylene monohydrate, which can be selectively produced by selecting catechol as the compound represented by the general formula (1) and selecting isolation and purification procedures mentioned later for the reaction solution after the aforementioned trimerization reaction, have superior thermal stability.

As the compound represented by the general formula (1) to be used in the present invention, that is, catechols, commercially available one or the one synthesized by a common procedure may be used as appropriate. In the present invention, as the compound represented by the general formula (1), in particular, catechol, in which two Rs in the general formula (1) are both hydrogen atoms, can be preferably used. In addition, the compound represented by the general formula (2) to be synthesized by using the catechol is 2,3,6,7,10,11-hexahydroxytriphenylene in which six Rs in the general formula (2) are all hydrogen atoms. Namely, the present invention is a particularly preferable production process as a process for synthesizing high-purity 2,3,6,7,10,11-hexahydroxytriphenylene, which is useful as a raw material of functional materials, with using inexpensive catechol as a raw material.

The metal oxide comprising a metal selected from trivalent iron, pentavalent vanadium and hexavalent molybdenum in the present invention is not especially limited, so long as the metal oxide contains trivalent iron, pentavalent vanadium or hexavalent molybdenum in its structure, and is an oxide of these metals having oxidizing property. Specifically, the metal oxide includes, for example, diiron trioxide (ferric oxide), triiron tetroxide, divanadium pentoxide, molybdenum trioxide, and the like, and among them, diiron trioxide (ferric oxide) is preferable. These metal oxides may be used alone or in a combination of two or more kinds. An amount of the metal oxide to be used is generally 1.0 to 10 equivalents, preferably 1.6 to 4 equivalents, as molar equivalent of trivalent iron, pentavalent vanadium or hexavalent molybdenum, relative to number of moles of the compound represented by the general formula (1). The metal oxides less than 1.0 equivalent will lead to decrease in yield of the desired compound represented by the general formula (2). On the other hand, these metal oxides in an amount exceeding 10 equivalents can be used, but result in such problems that economical efficiency is lost, and the like.

Thus, in the present invention, it has been found that the desired compound represented by the general formula (2) can be synthesized in high yield and in high purity by using a metal oxide comprising a metal selected from trivalent iron, pentavalent vanadium and hexavalent molybdenum. Further, it has been found that a crystal of monohydrate of the compound represented by the general formula (2) having a superior thermal stability can be produced by combining the aforementioned production process and the post-treatment procedures (isolation and purification procedures) to be mentioned later.

In addition, the nonvolatile strong acid in the present invention is not especially limited, so long as it is a nonvolatile strong acid which can dissolve the aforementioned metal oxide comprising a metal selected from trivalent iron, pentavalent vanadium and hexavalent molybdenum, and does not bring about variation in concentration during the reaction. Specifically, the nonvolatile strong acid includes, for example, inorganic acids such as sulfuric acid, nitric acid, phosphoric acid, and among them, sulfuric acid is preferable. These nonvolatile strong acids may be used alone or in a combination of two or more kinds, however, it is necessary to select a combination of nonvolatile strong acids each of which does not adversely affect on the compound represented by the general formula (1) as a raw material and the desired compound represented by the general formula (2). In addition, an amount of the nonvolatile strong acid to be used is not especially limited, so long as it is an amount sufficient to dissolve the metal oxide comprising a metal selected from trivalent iron, pentavalent vanadium and hexavalent molybdenum or more. Specifically, molar equivalent value of hydrogen ion in the nonvolatile strong acid, relative to number of moles of trivalent iron, pentavalent vanadium and hexavalent molybdenum in the metal oxide comprising a metal selected from trivalent iron, pentavalent vanadium and hexavalent molybdenum is generally 5 to 60 equivalents, and preferably 6 to 40 equivalents.

As the reaction solvent, as mentioned above briefly, water and/or a polar solvent can be used. The polar solvent cited here means a polar solvent, which can dissolve the compound represented by the general formula (1) as a raw material, and any polar solvent can be used so long as it does not show reduction action. Specifically, the polar solvent includes, for example, aprotic polar solvents such as acetonitrile, acetone, dimethylformamide, dimethylsulfoxide, and the like, and among them, dimethylformamide and dimethylsulfoxide are preferable. These reaction solvents may be used alone or in a combination of two or more kinds, and among them, preferably water is used alone. In addition, an amount of these reaction solvents to be used is an amount sufficient to dissolve the compound represented by the general formula (1) as a raw material or more, and may be set as appropriate so that a value of concentration in percent by weight of the nonvolatile strong acid in the reaction system becomes a proper concentration. Specifically, for example, molar equivalent of water and/or a polar solvent, relative to number of moles of the compound represented by the general formula (1) is generally 6 to 120 equivalents, and preferably 10 to 60 equivalents.

In the present invention, since reaction time and yield of the desired compound represented by the general formula (2) vary depending on a value of percent by weight of the nonvolatile strong acid in the reaction system, it is desirable that the reaction is conducted in a proper concentration. A proper value of the concentration in percent by weight of the nonvolatile strong acid in the reaction system varies depending on type of the nonvolatile strong acid and an amount thereof to be used, type of the reaction solvent and an amount thereof to be used, and the like, and it is difficult to determine unambiguously. Specifically, a concentration in percent by weight of the nonvolatile strong acid in the reaction system is in a range of generally 50 to 95%, preferably 60 to 90%, and more preferably 70 to 85%. Among them, when the nonvolatile strong acid is sulfuric acid, a concentration in percent by weight is in a range of preferably 60 to 90% and more preferably 70 to 85%. In particular, when the reaction is carried out in a range of 70 to 85%, the desired compound represented by the general formula (2) can be synthesized in a short time in a high yield hardly causing decomposition of the desired compound represented by the general formula (2) and the like. Also, as the nonvolatile strong acid, a commercially available one in the aforementioned range of concentration in percent by weight may be used as it is, or a diluted one may be used as appropriate.

Reaction temperature is desirably selected so that the compound represented by the general formula (1) can be efficiently trimerized, and specifically it is set in a range generally from 0 to 50° C., preferably from 20 to 45° C., and more preferably from 25 to 40° C. In particular, when the temperature is set in a range from 25 to 40° C., the desired compound represented by the general formula (2) can be synthesized in a short time in a high yield hardly causing decomposition of the desired compound represented by the general formula (2) and the like.

In the production process of the present invention, the reaction proceeds under any condition of normal pressure, pressurized and reduced pressure, but preferably the reaction is conducted under normal pressure where special facility is not needed.

Since reaction time may vary depending on molar equivalent number of trivalent iron, pentavalent vanadium and hexavalent molybdenum in the metal oxide comprising a metal selected from trivalent iron, pentavalent vanadium and hexavalent molybdenum, relative to the compound represented by the general formula (1), type of nonvolatile strong acid and an amount thereof to be used, type of reaction solvent and an amount thereof to be used, concentration in percent by weight of nonvolatile strong acid in the reaction system, reaction temperature, and the like, the reaction time cannot be determined unambiguously, but it is set in a range of generally 0.5 to 20 hours, and preferably 2 to 12 hours.

In the present invention, as a process for purifying the desired compound represented by the general formula (2) from the reaction solution after completion of the reaction, not only crystal can be purified but also two types of crystals can be selectively produced by employing the procedure described below. Specifically, two types of different crystals can be selectively produced by (a) dissolving the compound represented by the general formula (2) obtained by the production process of the present invention in a mixed solvent of acetone and water, and distilling off acetone from a obtained solution at a temperature in an appropriate range to precipitate crystal of the compound represented by the general formula (2), or by (b) dissolving the compound represented by the general formula (2) obtained by the production process of the present invention in a mixed solvent of acetone and water, and adding a water to a obtained solution at a temperature in an appropriate range to precipitate crystal of the compound represented by the general formula (2). Namely, two different types of crystals having superior thermal stability can be selectively produced by combining the production process of the present invention and further one of the crystal precipitation processes described above. In addition, the compound represented by the general formula (2) obtained by the production process of the present invention to be used for obtaining the desired crystal by a specific procedures as cited here, may be the one which is taken out by the common procedure from the reaction solution after completion of the reaction by the production process of the present invention, or the one of crude crystal. More specifically, for example, since crude crystal can be obtained by pouring the reaction solution after completion of the reaction into water, or pouring the water into the reaction solution and collecting the resultant precipitate by filtration, this crude crystal may be used. Alternatively, the crystal obtained by further washing the crude crystal with water and the like may be used, or the crystal further purified by column chromatography or the like may be used.

More specific crystal precipitation procedure of the aforementioned method (a) is as follows. For example, when the compound represented by the general formula (2) obtained by the production process of the present invention is crude crystal obtained by the aforementioned process, the crude crystal is dispersed in acetone, after that the dispersion liquid is stirred at room temperature, and filtered to filter off insoluble matter. Furthermore, activated charcoal is added to the filtrate, and the liquid is then stirred at room temperature, followed by filtering off the activated charcoal. To the filtrate obtained by such treatment, a specified amount of water is added to make a solution containing a mixed solvent of acetone and water, from which acetone is distilled off under normal pressure at a temperature in an appropriate range to precipitate a crystal. The crystal is collected by filtration and dried. The crystal can be precipitated (crystallized) in such way. Also, when crystallization is carried out using the crystal, which purified further the aforementioned crude crystal by column chromatography or the like, the dispersion treatment with acetone and the activated charcoal treatment are not necessarily carried out.

An amount of acetone to be used in the mixed solvent of acetone and water may be an amount sufficient to dissolve whole amount of the compound represented by the general formula (2). More specifically, an amount of acetone is, for example, generally around 2 mL or more, preferably around 3 to 100 mL, and more preferably around 5 to 60 mL per 1 g of the compound represented by the general formula (2) obtained by the production process of the present invention, which is a target of crystallization. When an excess amount of acetone is used, for example, in the aforementioned activated charcoal treatment, an amount of acetone to be used is desirably set in the aforementioned range by distilling off acetone before adding the water into the filtrate after the activated charcoal treatment.

An amount of water to be used in the mixed solvent of acetone and water may be an amount of such level that the compound represented by the general formula (2) dissolved in acetone does not precipitate in the water addition stage, but the crystal precipitates with distilling off acetone from the solution containing the mixed solvent of acetone and water. More specifically, a mixing ratio of water is, for example, generally around 10 to 500 mL, preferably around 30 to 300 mL, and more preferably around 50 to 200 mL per 100 mL of acetone in the mixed solvent of acetone and water. When water is added to the filtrate, for example, after the aforementioned activated charcoal treatment, an amount of water to be added is desirably adjusted so that the mixing ratio of acetone and water falls in the aforementioned range.

In the method (a) of the present invention, acetone is distilled off in obtaining the crystal, and this distilling off is carried out under normal pressure. Therefore, temperature when acetone is distilled off from the solution containing the mixed solvent of acetone and water is set at generally 56° C. or higher, and preferably at a temperature in a range from 56 to 95° C. In the precipitation method (a), the crystal having the desired crystal form is desirably crystallized at 70° C. or higher. In addition, since the compound represented by the general formula (2) has a property that it is soluble in acetone but insoluble in water, in order to precipitate crystal by distilling off acetone from the solution containing the mixed solvent, distilling off of acetone starts at 56° C., which is a boiling point of acetone under normal pressure, or higher, and crystallization is performed at 70° C. or higher and practically completed within a temperature range from 70 to 80° C. Also, when crystallization can be done at 70° C. or higher, acetone may be distilled off generally at 70° C. or higher, and preferably at a temperature in a range from 70 to 80° C.

As mentioned above briefly, the crystal precipitated in such way may be isolated by a common procedure. Specifically, the crystal having the desired crystal form can be obtained, for example, by collecting the crystal by a filtration means such as suction filtration, followed by drying the obtained crystal under reduced pressure.

On the other hand, more specific crystal precipitation procedure (purifying method) of the aforementioned method (b) is as follows. For example, when the compound represented by the general formula (2) obtained by the production process of the present invention is crude crystal obtained by the aforementioned process, the crude crystal is dispersed in acetone, after that the dispersion liquid is stirred at room temperature, and filtered to filter off insoluble matter. Furthermore, activated charcoal is added to the filtrate, and the liquid is then stirred at room temperature, followed by filtering off the activated charcoal. The filtrate obtained by such treatment is once evaporated to dryness by condensing and distilling off acetone under reduced pressure, and then specified amounts of acetone and water are added to the resultant residue. A crystal is precipitated by adding the water to the obtained solution containing the mixed solvent of acetone and water at a temperature in an appropriate range, collected by filtration, and then dried. The crystal can be precipitated (crystallized) in such way. Also, when crystallization is carried out using the crystal which purified further the aforementioned crude crystal by column chromatography or the like, the dispersion treatment with acetone and the activated charcoal treatment are not necessarily carried out.

An amount of acetone to be used in the mixed solvent of acetone and water may be an amount sufficient to dissolve whole amount of the compound represented by the general formula (2). More specifically, an amount of acetone is, for example, generally around 1 to 30 mL, preferably around 1.5 to 20 mL, and more preferably around 2 to 10 mL per 1 g of the compound represented by the general formula (2) obtained by the production process of the present invention, which is a target of crystallization. In order to precipitate crystal efficiently, the compound represented by the general formula (2) is dissolved desirably using as small amount as possible of acetone.

An amount of water to be used in the mixed solvent of acetone and water may be an amount of such level that the compound represented by the general formula (2) dissolved in acetone does not precipitate. More specifically, a mixing ratio of water is, for example, generally around 5 to 100 mL, preferably around 10 to 90 mL, and more preferably around 20 to 80 mL per 100 mL of acetone in the mixed solvent of acetone and water. Thus, the compound represented by the general formula (2) can be effectively dissolved by using the mixed solvent of acetone and water by adding an appropriate amount of water to acetone.

An amount of water to be added to the solution containing the mixed solvent of acetone and water may be an amount of such level that the compound represented by the general formula (2) dissolved in the mixed solvent of acetone and water precipitates by the addition of water. More specifically, an additional ratio of water is, for example, generally around 200 to 2000 mL, preferably around 250 to 1500 mL, and more preferably around 300 to 1200 mL per 100 mL of acetone in the mixed solvent of acetone and water.

Temperature at which water is added to the solution containing the mixed solvent of acetone and water should be set at a temperature at which the crystal having the desired crystal form precipitates, and specifically, set at a temperature in a range generally from 5 to 50° C., and preferably from 10 to 35° C. In the precipitation method (b), since the crystal having the desired crystal form is desirably crystallized at 50° C. or lower, in addition, the compound represented by the general formula (2) has a property that it is soluble in acetone but insoluble in water, in order to precipitate crystal to precipitate by adding a water to the solution containing the mixed solvent, crystallization is carried out while the solution kept at 50° C. is slowly cooled down to 5° C. and kept at this temperature, in particular, crystallization is preferably completed within a temperature range from 10 to 35° C.

As mentioned above briefly, the crystal precipitated in such way may be isolated by a common procedure. Specifically, the crystal having the desired crystal form can be obtained, for example, by collecting the crystal by a filtration means such as suction filtration, followed by drying the filtered crystal under reduced pressure.

As mentioned above, two types of crystals having the different crystal forms can be produced by combining the production process of the present invention and further the crystal precipitation procedure (crystallization method). When a crude crystal is crystallized, purification can be done simultaneously by this procedure.

Also, in the isolation and purification procedures, when a crystal form of the compound represented by the general formula (2) to be obtained need not to be considered, any one among the well-known isolation and purification procedures can be employed. More specifically, for example, reaction solution is poured into water, or water is poured into reaction solution, the resultant precipitate is collected by filtration, and then collected crude crystal is washed with water. Thereafter, the crude crystal is dispersed in a mixed solvent of water and a suitable polar solvent, and the dispersion liquid is heated up to a specified temperature with stirring, then filtered in hot state at the same temperature. The filtrate is concentrated and precipitated crystal is collected by filtration. The crystal can be purified efficiently in such way.

In the isolation and purification procedures, the polar solvent to be used for dispersing the crude crystal includes, for example, an aprotic polar solvent such as acetonitrile, acetone. In addition, in the filtration in hot state, a filter aid such as diatom earth, activated charcoal may be used in combination.

As mentioned above, in the production process of the present invention, even when any of the isolation and purification procedures described above is employed, any metal including iron and the like used in the reaction can be removed. Further, according to the present invention, since oxidizing agent such as organic peroxide is not used, complicated steps such as reduction, liquid separation and extraction to remove excess organic peroxide are not required as a posttreatment procedure, and the desired compound represented by the general formula (2) can be isolated and purified by easy and simple procedures.

In addition, in the production process of the present invention, a crystal of 2,3,6,7,10,11-hexahydroxytriphenylene monohydrate having superior thermal stability can be produced by crystallizing 2,3,6,7,10,11-hexahydroxytriphenylene which is obtained by using catechol as the compound represented by the general formula (1) employing any one among the crystallization procedures of the method (a) and method (b) described above. More specifically, when 2,3,6,7,10,11-hexahydroxytriphenylene obtained by the production process of the present invention is crystallized according to the method (a), type B' crystal of 2,3,6,7,10,11-hexahydroxytriphenylene monohydrate can be produced, and when 2,3,6,7,10,11-hexahydroxytriphenylene obtained by the production process of the present invention is crystallized according to the method (b), type C crystal of 2,3,6,7,10,11-hexahydroxytriphenylene monohydrate can be produced. Furthermore, the type B' crystal and the type C crystal of the monohydrate obtained by the aforementioned method (a) and method (b), respectively, are both superior in thermal stability.

Namely, the present inventors have found that type B' crystal and type C crystal of 2,3,6,7,10,11-hexahydroxytriphenylene monohydrate, both having more superior thermal stability compared to that of type B crystal of the monohydrate obtained by existing production process, can be obtained by further crystallizing 2,3,6,7,10,11-hexahydroxytriphenylene obtained by the production process of the present invention using a specific crystallization method. More specifically, the present inventors have disclosed for the first time that although the well-known type B crystal of 2,3,6,7,10,11-hexahydroxytriphenylene monohydrate is inferior in thermal stability, the crystal of the monohydrate obtained by the production process of the present invention further combined with a specific crystallization method, that is, a specific recrystallization method, is superior in thermal stability. In addition, the present inventors have found, as a result of intensive studies, that the type C crystal of 2,3,6,7,10,11-hexahydroxytriphenylene monohydrate having superior thermal stability is a novel one. As mentioned above, the present invention has been completed based on such knowledge.

The type B' crystal of 2,3,6,7,10,11-hexahydroxytriphenylene obtained according to the process (crystallization method) of the present invention is composed of 2,3,6,7,10,11-hexahydroxytriphenylene monohydrate, and it has been identified by Karl-Fischer method that the type B' crystal is monohydrate.

In addition, the type B' crystal of 2,3,6,7,10,11-hexahydroxytriphenylene monohydrate has main peaks at 11.4, 17.2, 22.6, 26.1 and 27.7 in Bragg angle (2θ±0.2°) in a X-ray diffraction spectrum for CuKα characteristic X-ray (wavelength: 1.5418 Å), and these data are similar to the X-ray data of the type B crystal of 2,3,6,7,10,11-hexahydroxytriphenylene monohydrate described, for example, in WO2005/090275. However, since the type B' crystal according to the present invention is more superior in thermal stability compared with the well-known type B crystal, and further, the well-known type B crystal has a thermal decomposition temperature (Td) at about 162° C. whereas the type B' crystal according to the present invention has no thermal decomposition temperature (Td), though details are not clear, it is suggested that the type B' crystal according to the present invention is a compound which has a structure based on the physical properties different from those of the well-known type B crystal.

The type C crystal from 2,3,6,7,10,11-hexahydroxytriphenylene obtained according to the process (crystallization method) of the present invention is composed of 2,3,6,7,10,11-hexahydroxytriphenylene monohydrate, and it has been identified by Karl-Fischer method that the type C crystal is monohydrate.

In addition, the type C crystal of 2,3,6,7,10,11-hexahydroxytriphenylene monohydrate has main peaks at 9.3, 10.2 and 26.4 in Bragg angle (2θ±0.2°) in a X-ray diffraction spectrum for CuKα characteristic X-ray (wavelength: 1.5418 Å), and does not have any peak between 10.5 and 12.5 in Bragg angle (2θ±0.2°) (this means in other words "any peak cannot be clearly identified in this range"), and further, thermal analysis (TG/DTA) of the type C crystal reveals that the type C crystal is a novel crystal with a thermal decomposition temperature (Td) at 140° C., and more superior in thermal stability compared with the well-known type B crystal.

Hereinafter, the present invention will be specifically explained referring to Examples, but the present invention is not limited thereto by any means.

EXAMPLES

Example 1

Synthesis of 2,3,6,7,10,11-hexahydroxytriphenylene Using Catechol as a Starting Material and Diiron Trioxide (Ferric Oxide) as a Metal Oxide Comprising a Trivalent Iron Catechol (22.0 g, 0.2 moles) and diiron trioxide (ferric oxide) (31.9 g, 0.2 moles) were added into water (110 mL), and 98% sulfuric acid (440 g, 4.4 moles) was added dropwise to the solution while temperature of the solution was maintained at 30° C. or lower, to adjust the concentration in percent by weight of sulfuric acid in the reaction system at 80%. The solution was reacted at 30° C. for 6 hours with stirring. After completion of the reaction, water (500 mL) was added dropwise to the reaction solution, and the reaction solution was stirred for another 30 minutes. The resultant precipitate was collected by filtration, and the obtained crude crystal was washed with water and dried to give crude crystal (19.2 g). After a part of the crude crystal (5.0 g among 19.2 g) was dispersed in a mixed solvent of water (50 mL) and acetonitrile (200 mL), the dispersion liquid was heated up and stirred for 1 hour. After that, this dispersion liquid was filtered in hot state to filter off insoluble matter, the filtrate was then concentrated under reduced pressure, and the precipitated crystal was collected by filtration, and then dried, to give 2,3,6,7,10,11-hexahydroxytriphenylene (2.56 g, theoretical yield from catechol: 45.5%) in black powder form. $^1$H-NMR data of the obtained 2,3,6,7,10,11-hexahydroxytriphenylene measured were in accordance with those of 2,3,6,7,10,11-hexahydroxytriphenylene described in the reference. Also, the measurement results of $^1$H-NMR are shown below. In addition, content of iron ion in the obtained crystal was measured by inductively-coupled plasma optical emission spectroscopy (ICP-OES), and was found that content of iron ion (reduced quantity from metal iron) in the obtained 2,3,6,7,10,11-hexahydroxytriphenylene (2.56 g) was 0.087 mg (0.034 mg/g). Also, the measurement of iron ion content by inductively-coupled plasma optical emission spectroscopy was carried out using inductively-coupled plasma optical emission spectrometer SPS 3100 (manufactured by SII Nanotechnology Inc.) as follows. Several samples containing appropriate amount of metal iron dissolved in n-methyl-2-pyrrolidone were measured and a calibration curve were obtained based on the measurement results, in advance. Content of iron ion in 2,3,6,7,10,11-hexahydroxytriphenylene was obtained from the calibration curve.

$^1$H-NMR (400 MHz, DMSO-d6) δ (ppm): 7.61 (s, Ar), 9.27 (s, OH).

Example 2

Synthesis of 2,3,6,7,10,11-hexahydroxytriphenylene Using Catechol as a Starting Material and Divanadium Pentoxide (Vanadium (V) Oxide) as a Metal Oxide Comprising Pentavalent Vanadium Catechol (22.0 g, 0.2 moles) and divanadium pentoxide (vanadium (V) oxide) (36.4 g, 0.2 moles) were added into water (110 mL), and 98% sulfuric acid (440 g, 4.4 moles) was added dropwise to the solution while temperature of the solution was maintained at 30° C. or lower, to adjust the concentration in percent by weight of sulfuric acid in the reaction system at 80%. The solution was reacted at 30° C. for 6 hours with stirring. After completion of the reaction, water (500 mL) was added dropwise to the reaction solution while temperature of the solution was maintained at 30° C. or lower, and the reaction solution was stirred at the same temperature for another 30 minutes. The resultant precipitate was collected by filtration, and the obtained crude crystal was washed with water. The crude crystal was further dispersed in water (1 L), and the dispersion liquid was stirred for 30 minutes, and then filtered to collect crystal. After the collected crystal was dispersed in acetone (400 mL), the dispersion liquid was stirred for 30 minutes. After that, the dispersion liquid was filtered to filter off insoluble matter, and the filtrate was concentrated under reduced pressure to distill off an excess amount of acetone. Subsequently, water (160 mL) was poured into the concentrated filtrate (solution of about 160 mL). This solution was slowly heated up from 56° C. under normal pressure to concentrate the solution. Crystal precipitated when temperature of the concentrated solution became 70 to 80° C. Concentration was further continued, and stopped when temperature of the concentrated solution became 90° C. The crystal thus precipitated was collected by filtration, and then dried, to give 2,3,6,7,10,11-hexahydroxytriphenylene (7.27 g, theoretical yield from catechol: 33.6%) in black powder form. Also, the obtained compound in black powder form was identified to be 2,3,6,7,10,11-hexahydroxytriphenylene by measuring $^1$H-NMR in the same way as in Example 1.

Example 3

Synthesis of 2,3,6,7,10,11-hexahydroxytriphenylene Using Catechol as a Starting Material and Molybdenum Trioxide (Molybdenum (VI) Oxide) as a Metal Oxide Comprising Hexavalent Molybdenum Catechol (22.0 g, 0.2 moles) and molybdenum trioxide (molybdenum (VI) oxide) (57.54 g, 0.4 moles) were added into water (110 mL), and 98% sulfuric acid (440 g, 4.4 moles) was added dropwise to the solution while temperature of the solution was maintained at 30° C. or lower, to adjust the concentration in percent by weight of sulfuric acid in the reaction system at 80%. The solution was reacted at 30° C. for 6 hours with stirring. Reaction rate after reacting for 6 hours was 18.0%. Also, the reaction rate was determined by taking out a part of the solution after reacting for 6 hours and measuring the solution by high performance liquid chromatography (HPLC). In addition, the peak detected by high performance liquid chromatography (HPLC) was confirmed to be 2,3,6,7,10,11-hexahydroxytriphenylene by the fact that it corresponded to the peak of 2,3,6,7,10,11-hexahydroxytriphenylene obtained by the existing process. Namely, the compound obtained in Example 3 was identified to be 2,3,6,7,10,11-hexahydroxytriphenylene by the fact that the retention time in HPLC of the compound obtained in Example 3 was in accordance with the retention time in HPLC of 2,3,6,7,10,11-hexahydroxytriphenylene obtained by the existing process. Also, identification by high performance liquid chromatography (HPLC) was carried out under the following conditions: Intelligent HPLC Pump Model PU-980 and Intelligent UV/VIS Detector Model UV-970 (manufactured by JASCO Corp.), Column: Wakosil-II 5C-18, 4.6 mm×150 mm (Wako Pure Chemical Industries, Ltd.), Eluent: Acetonitrile/Water/Phosphoric Acid/Triethylamine=200 mL/800 mL/2 mL/2 mL, Measurement Wavelength: 275 nm. In addition, the aforementioned reaction rate was determined as follows. Firstly, several samples containing appropriate amounts of 2,3,6,7,10,11-hexahydroxytriphenylene dissolved in the above eluent were measured using the aforementioned HPLC instrument and the like to obtain peak areas, and a calibration curve was obtained based on the peak areas, in advance. The reaction rate was calculated by comparing the peak area in HPLC measurement of the solution after reaction (an amount of the solution after reaction taken out was converted to an amount of whole solution after reaction) and that of the calibration curve, and by determining an abundance of 2,3,6,7,10,11-hexahydroxytriphenylene in the solution after reaction.

Example 4

Synthesis of Type B' Crystal of 2,3,6,7,10,11-hexahydroxytriphenylene monohydrate Using Catechol as a Starting Material and Diiron Trioxide (Ferric Oxide) as a Metal Oxide Comprising Trivalent Iron Catechol (22.0 g, 0.2 moles) and diiron trioxide (ferric oxide) (31.9 g, 0.2 moles) were added into water (44 mL), and 98% sulfuric acid (176 g, 1.76 moles) was added dropwise to the solution while temperature of the solution is maintained at 30° C. or lower, to adjust the concentration in percent by weight of sulfuric acid in the reaction system at 80%. The solution was reacted at 30° C. for 6 hours with stirring. After completion of the reaction, water (200 mL) was added dropwise to the reaction solution while temperature of the solution was maintained at 30° C. or lower, and the reaction solution was stirred at the same temperature for another 30 minutes. The resultant precipitate was collected by filtration, and the obtained crude crystal was washed with water. The crude crystal was further dispersed in water (400 mL), and the dispersion liquid was stirred for 30 minutes, and then filtered to collect crystal. After the collected crystal was dispersed in acetone (400 mL), the dispersion liquid was stirred for 30 minutes. After that, the dispersion liquid was filtered to filter off insoluble matter, and activated charcoal (10.81 g) was added to the filtrate, which was then stirred for 30 minutes. After stirring, the filtrate was concentrated under reduced pressure to distill off an excess amount of acetone. Subsequently, water (160 mL) was poured into the concentrated filtrate (solution of about 160 mL). This solution was slowly heated up from 56° C. under normal pressure to concentrate the solution. Crystal precipitated when temperature of the concentrated solution became 70 to 80° C. Concentration was further continued, and stopped when temperature of the concentrated solution became 90° C. The crystal thus precipitated was collected by filtration, and then dried, to give type B' crystal of 2,3,6,7,10,11-hexahydroxytriphenylene monohydrate (9.32 g, theoretical yield from catechol: 40.8%) in dark yellow powder form. Also, water content of the obtained the type B' crystal was measured using a Karl-Fischer measuring instrument (Moisture Meter KF-200, manufactured by Mitsubishi Chem. Corp.), and found to be 5.5%. On the other hand, since molecular weight of 2,3,6,7,10,11-hexahydroxytriphenylene monohydrate was 342.30 ($C_{18}H_{12}O_6.H_2O$) and that of water was 18.02, and also theoretical water content of 2,3,6,7,10,11-hexahydroxytriphenylene monohydrate was 5.26%, the obtained type B' crystal was confirmed to be monohydrate of 2,3,6,7,10,11-hexahydroxytriphenylene.

Example 5

Synthesis of Type C Crystal of 2,3,6,7,10,11-hexahydroxytriphenylene monohydrate Using Catechol as a Starting Material and Diiron Trioxide (Ferric Oxide) as a Metal Oxide Comprising Trivalent Iron Catechol (22.0 g, 0.2 moles) and diiron trioxide (ferric oxide) (31.9 g, 0.2 moles) were added into water (44 mL), and 98% sulfuric acid (176 g, 1.76 moles) was added dropwise to the solution while temperature of the solution is maintained at 30° C. or lower, to adjust the concentration in percent by weight of sulfuric acid in the reaction system at 80%. The solution was reacted at 30° C. for 6 hours with stirring. After completion of the reaction, water (200 mL) was added dropwise to the reaction solution while temperature of the solution was maintained at 30° C. or lower, and the reaction solution was stirred at the same temperature for another 30 minutes. The resultant precipitate was collected by filtration, and the obtained crude crystal was washed with water. The crude crystal was further dispersed in water (400 mL), and the dispersion liquid was stirred for 30 minutes, and then filtered to collect crystal. After the collected crystal was dispersed in acetone (400 mL), the dispersion liquid was stirred for 30 minutes. After that, the dispersion liquid was filtered to filter off insoluble matter, and activated charcoal (10.81 g) was added to the filtrate, which was then stirred for 30 minutes. After stirring, the filtrate was concentrated under reduced pressure to distill off acetone, and evaporated to dryness. After the residue after evaporation to dryness was dissolved by adding the acetone (40 mL) and the water (20 mL) thereto at room temperature, water (380 mL) was slowly added dropwise at the same temperature. By cooling down the solution after the addition to 10° C., crystal precipitated. The crystal thus precipitated was collected by filtration, and then dried, to give type C crystal of 2,3,6,7,10,11-hexahydroxytriphenylene monohydrate (8.43 g, theoretical yield from catechol: 36.9%) in reddish purple powder form. Also, water content of the obtained the type C crystal was measured by Karl-Fischer method in the same way as in Example 4, and the type C crystal was confirmed to be monohydrate of 2,3,6,7,10,11-hexahydroxytriphenylene.

Example 6

Measurement of X-Ray Powder Diffraction Spectra of Type B' and Type C Crystals of 2,3,6,7,10,11-hexahydroxytriphenylene monohydrate Obtained in Examples 4 and 5

Figure 2:
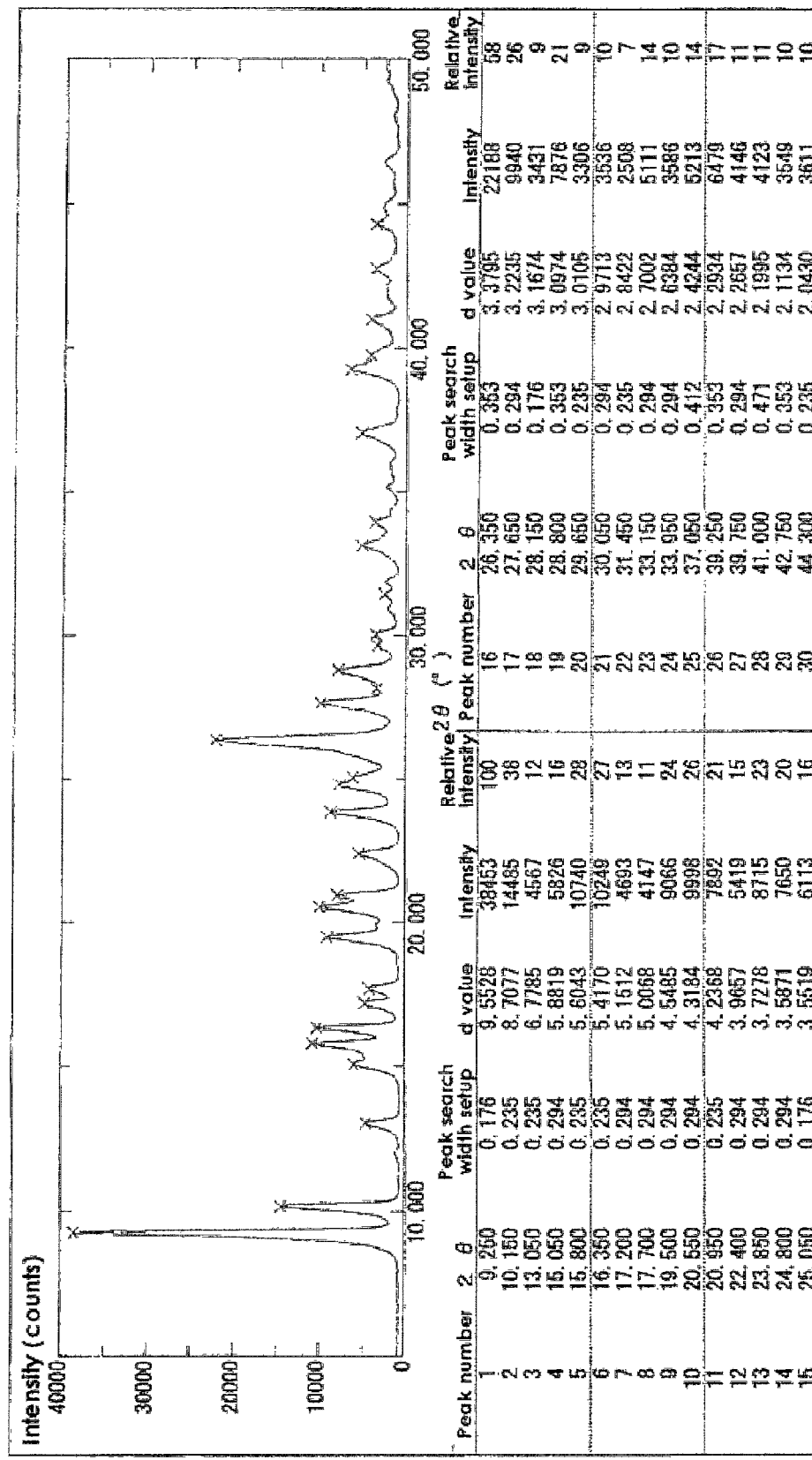
FIG. 2 is a figure showing an X-ray diffraction spectrum of type C crystal of 2,3,6,7,10,11-hexahydroxytriphenylene monohydrate obtained in Example 5.

Measurement of X-ray powder diffraction spectra of type B' and type C crystals of 2,3,6,7,10,11-hexahydroxytriphenylene monohydrate obtained was carried out using RINT 2000/PC (manufactured by Rigaku Corp.), and Cu radiation having $\lambda=1.5418$ Å through a monochromator, to obtain X-ray diffraction spectra. The measurement results for the type B' crystal and for the type C crystal are shown in FIG. 1 and FIG. 2, respectively, and also, values of main peaks in these spectra are shown in Table 1 (peak data for the type B' crystal) and Table 2 (peak data for the type C crystal), respectively.

TABLE 1

| $2\theta$ | d | Relative intensity ($I/I_0$) |
|---|---|---|
| 11.350 | 7.7896 | 0.21 |
| 17.150 | 5.1661 | 0.38 |
| 18.200 | 4.8703 | 0.11 |
| 22.600 | 3.9311 | 0.39 |
| 26.050 | 3.4178 | 0.20 |
| 27.650 | 3.2235 | 1.00 |
| 28.300 | 3.1509 | 0.11 |
| 29.150 | 3.0610 | 0.14 |
| 33.800 | 2.6497 | 0.11 |
| 44.800 | 2.0214 | 0.13 |

TABLE 2

| $2\theta$ | d | Relative intensity ($I/I_0$) |
|---|---|---|
| 9.250 | 9.5528 | 1.00 |
| 10.150 | 8.7077 | 0.38 |
| 15.800 | 5.6043 | 0.28 |
| 16.350 | 5.4170 | 0.27 |
| 19.500 | 4.5485 | 0.24 |
| 20.550 | 4.3184 | 0.26 |
| 23.850 | 3.7278 | 0.23 |
| 26.350 | 3.3795 | 0.58 |
| 27.650 | 3.2235 | 0.26 |

Example 7

Measurement of Thermometric Analyses (TG/DTA) of Type B' and Type C Crystals of 2,3,6,7,10,11-hexahydroxytriphenylene monohydrate Obtained in Examples 4 and 5

Figure 3:
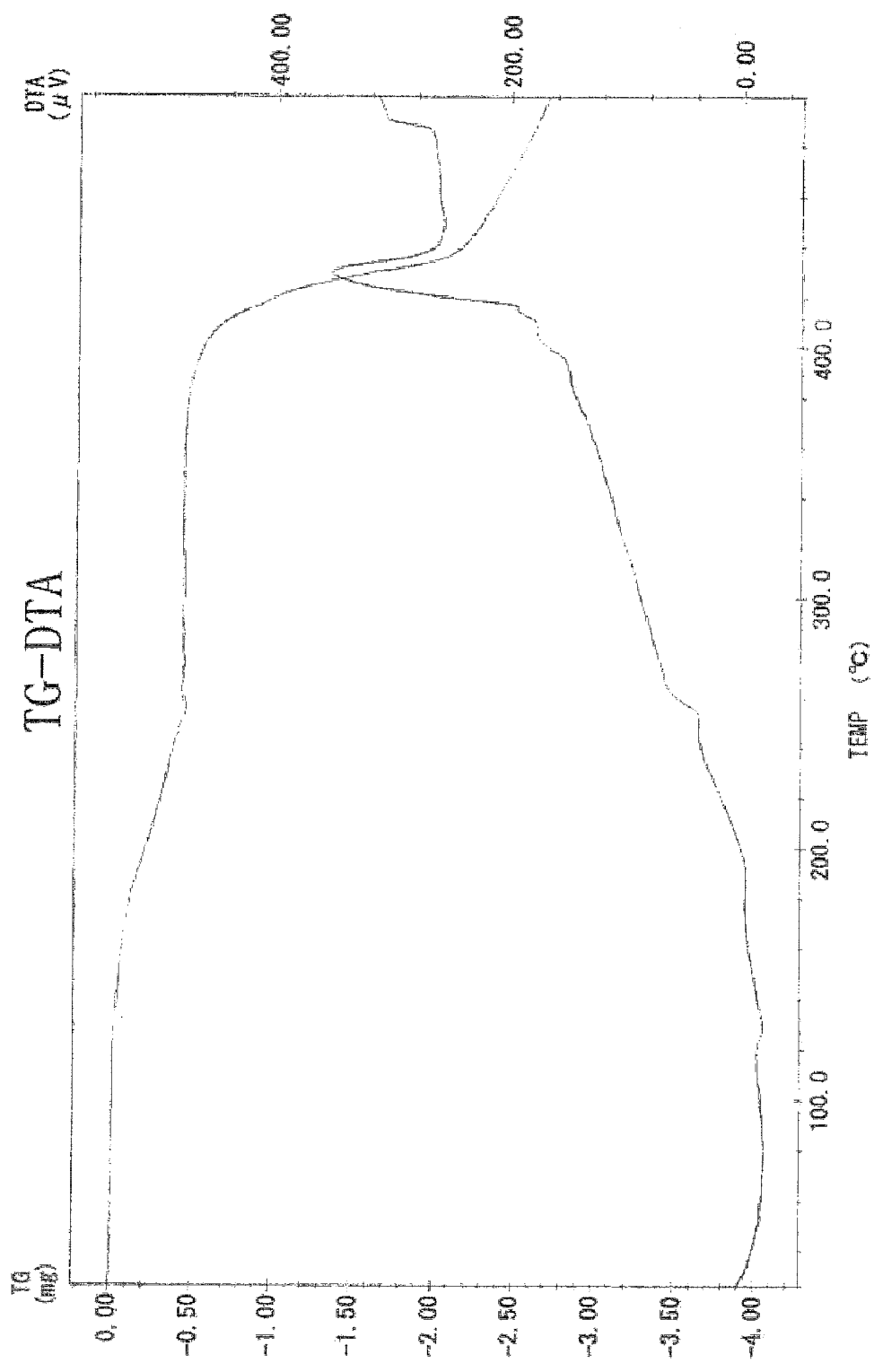
FIG. 3 is a figure showing a thermometric analysis (TG/DTA) data of type B' crystal of 2,3,6,7,10,11-hexahydroxytriphenylene monohydrate obtained in Example 4.
Figure 4:
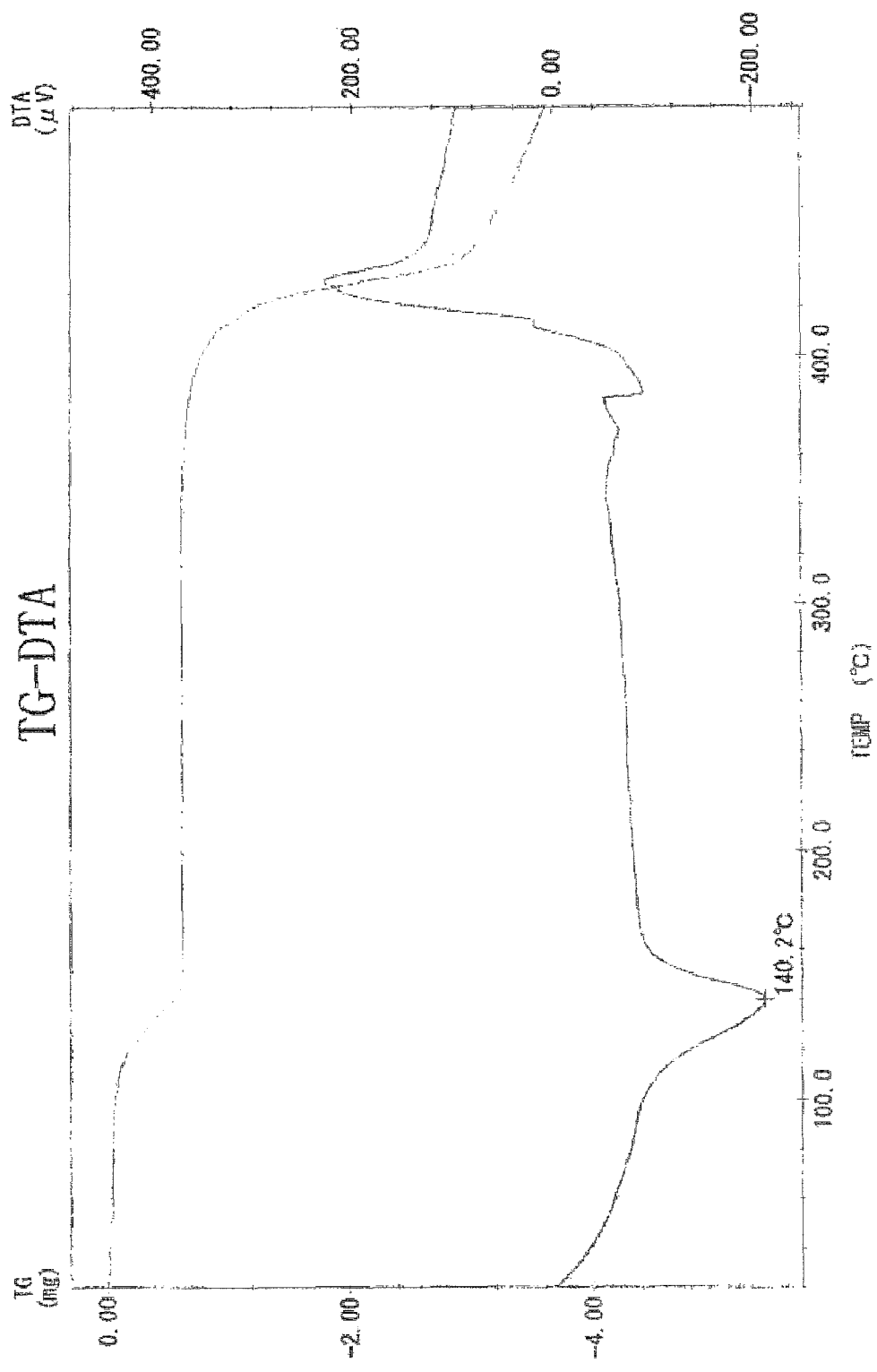
FIG. 4 is a figure showing a thermometric analysis (TG/DTA) data of type C crystal of 2,3,6,7,10,11-hexahydroxytriphenylene monohydrate obtained in Example 5.

Measurement of thermometric analyses (TG/DTA) of the type B' and the type C crystals of 2,3,6,7,10,11-hexahydroxytriphenylene monohydrate obtained was carried out using thermometric analyzer TAPS 3000S manufactured by Bruker AXS Corp. under the following conditions: measuring temperature range: 30 to 500° C., temperature rising rate: 10° C./minute, carrier gas: argon gas (100 mL/minute). About 10 mg of the crystal to be analyzed was weighed on the aluminum-made shallow dish, which was placed on a sample dish of the analyzer, and subjected to the measurement under the aforementioned conditions. Also, as a reference, about 10 mg of $\alpha Al_2O_3$ was used. As the results of the measurement, the type B' Crystal of 2,3,6,7,10,11-hexahydroxytriphenylene monohydrate was found to have no thermal decomposition temperature (Td), but the type C crystal was found to have thermal decomposition temperature (Td) at 140° C. The measurement results of thermometric analyses of the type B' crystal is shown in FIG. 3, and the measurement results of thermometric analyses of the type C crystal is shown in FIG. 4.

Comparative Example 1

Synthesis of Type B Crystal of 2,3,6,7,10,11-hexahydroxytriphenylene monohydrate by an Existing Process A type B crystal of 2,3,6,7,10,11-hexahydroxytriphenylene monohydrate was synthesized according to the process described in Synthesis, 477, 1994 and JP-A-8-119894. Namely, 1,2-dimethoxybenzene (31.78 g, 0.23 moles) and anhydrous ferric chloride (120 g, 0.74 moles) were dissolved in 70% sulfuric acid, and the solution was reacted at 25° C. for 24 hours with stirring. After completion of the reaction, the solution was poured into ice water (500 g), and the precipitated crystal was collected by filtration. After the resultant crystal was washed with water (1 L), and then dried to give pale purple colored 2,3,6,7,10,11-hexamethoxytriphenylene (28.2 g, theoretical yield from 1,2-dimethoxybenzene: 90.1%) (the method of Synthesis, 477, 1994).

Subsequently, to the obtained 2,3,6,7,10,11-hexamethoxytriphenylene (28.2 g, 0.069 moles), 57% hydroiodic acid (235.3 g, 1.05 moles) and acetic acid (145 mL) were added, and the solution was refluxed for 2 hours. After completion of the reaction, the solution was cooled down to room temperature, and the precipitated crystal was collected by filtration.

Figure 5:
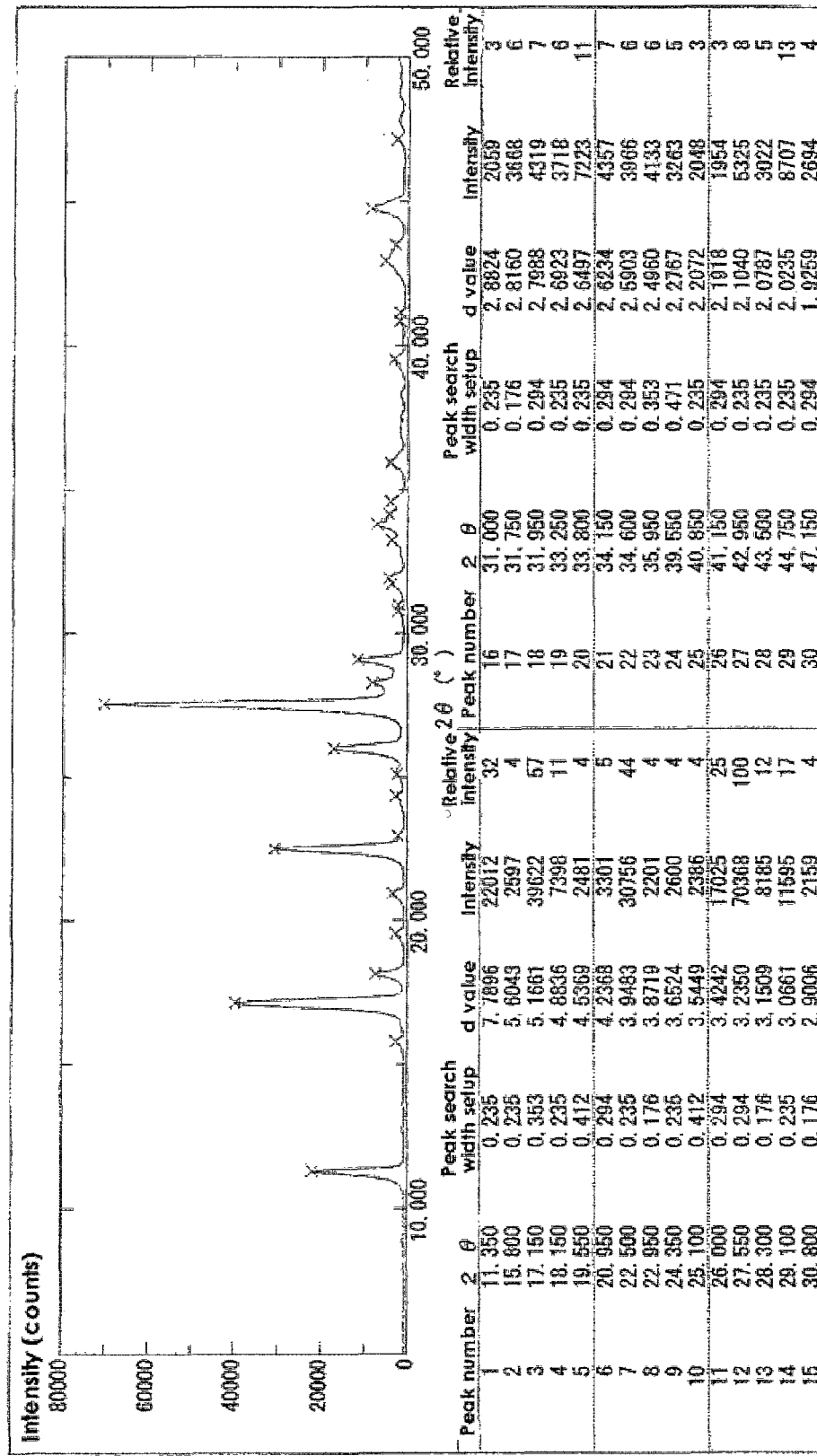
FIG. 5 is a figure showing an X-ray diffraction spectrum of type B crystal of 2,3,6,7,10,11-hexahydroxytriphenylene monohydrate obtained in Comparative Example 1.

The crystal collected by filtration was dried under reduced pressure to give gray type B crystal of 2,3,6,7,10,11-hexahydroxytriphenylene monohydrate (20.2 g, yield: 85.5%) (the method of JP-A-8-119894). Also, the resultant gray compound was confirmed to be 2,3,6,7,10,11-hexahydroxytriphenylene monohydrate by $^1$H-NMR analysis and measurement of water content by Karl-Fischer measuring instrument. In addition, the measurement results of X-ray powder diffraction spectrum of the type B crystal are shown in FIG. 5 and also, main peak values of the type B crystal are shown in Table 3. Also, the measurement of X-ray powder diffraction spectrum was carried out in the same way as in Example 6.

TABLE 3

| 2θ | d | Relative intensity (I/I$_0$) |
|---|---|---|
| 11.350 | 7.7896 | 0.32 |
| 17.150 | 5.1661 | 0.57 |
| 18.150 | 4.8836 | 0.11 |
| 22.500 | 3.9483 | 0.44 |
| 26.000 | 3.4242 | 0.25 |
| 27.550 | 3.2350 | 1.00 |
| 28.300 | 3.1509 | 0.12 |
| 29.100 | 3.0661 | 0.17 |
| 33.800 | 2.6497 | 0.11 |
| 44.750 | 2.0235 | 0.13 |

Experimental Example 1

Thermal Stability Test for Type B' Crystal, Type C Crystal and Type B Crystal of 2,3,6,7,10,11-hexahydroxytriphenylene Monohydrate Obtained in Examples 4 and 5, and Comparative Example 1

Each of type B' crystal, type C crystal and type B crystal of 2,3,6,7,10,11-hexahydroxytriphenylene monohydrate obtained in Examples 4 and 5, and Comparative Example 1 (50 mg each) was dissolved in methanol and total volume of each solution was adjusted to 100 mL, to prepare methanol solution of each crystal. Visible-ultraviolet spectroscopy was measured by filling a quartz cell with the methanol solution and using methanol as a reference. Measurement by visible-ultraviolet spectroscopy was carried out using ultraviolet-visible spectrophotometer UV-2550 manufactured by Shimadzu Corp. as a visible-ultraviolet spectrometry instrument and a quartz cell having an optical path length of 10 mm, by measuring the absorbance at 360 nm and 520 nm.

In addition, each of quartz cells used in the measurement was left to stand in a thermostatic chamber maintained at 60° C. for predetermined days, and on the cells left stand for predetermined days, absorbance at 360 nm and 520 nm was measured in the same way as described above. The results are shown in Table 4.

TABLE 4

| | Entry | | |
|---|---|---|---|
| Crystal form | 1 (Example 4) Type B' crystal | 2 (Example 5) Type C crystal | 3 (Comparative Example 1) Type B crystal |
| 0$^{th}$ day 520 nm | 0.021 | 0.021 | 0.029 |
| 0$^{th}$ day 360 nm | 0.640 | 0.651 | 0.777 |
| 7$^{th}$ day 520 nm | 0.030 | 0.015 | 0.063 |
| 7$^{th}$ day 360 nm | 0.643 | 0.642 | 0.797 |
| 14$^{th}$ day 520 nm | 0.025 | 0.017 | 0.099 |
| 14$^{th}$ day 360 nm | 0.642 | 0.680 | 0.845 |
| 21$^{th}$ day 520 nm | 0.028 | 0.016 | 0.134 |
| 21$^{th}$ day 360 nm | 0.652 | 0.695 | 0.888 |

From the results in Table 4, since the type B' crystal and the type C crystal of 2,3,6,7,10,11-hexahydroxytriphenylene monohydrate obtained in Examples 4 and 5 show little difference even after leaving stand for 21 days at 60° C. in any of the values of absorbance at 360 nm and 520 nm, it can be understood that these crystals hardly change even at 60° C., and are superior in thermal stability. On the other hand, since the type B crystal of the well-known 2,3,6,7,10,11-hexahydroxytriphenylene monohydrate obtained in Comparative Example 1 shows increases in both of the values of absorbance at 360 nm and 520 nm by leaving stand at 60° C. for 21 days, and also in visual observation, the methanol solutions shows significant discoloration by the day, it can be understood that this type B crystal is inferior in thermal stability causing some change at 60° C. Also, as obvious from the measurement results of iron ion content in Example 1, it is considered to be contributing to the thermal stability of the monohydrate crystal that little amount of metal oxide of iron and the like is contained in 2,3,6,7,10,11-hexahydroxytriphenylene obtained by the production process of the present invention.

As mentioned above, from the results of Examples 1 to 3, it can be understood that a high-purity desired compound represented by the general formula (2) can be isolated and purified with easy and simple procedures such as recrystallization in high yield by conducting the reaction in the presence of a metal oxide comprising a metal selected from trivalent iron, pentavalent vanadium and hexavalent molybdenum and of a nonvolatile strong acid. When ferric (III) chloride is used as in the existing process, a reduction step is required to reduce an iron complex and/or quinone derivative of the compound represented by the general formula (2). Whereas in the production process of the present invention in which a metal oxide of a specified metal is used in the reaction, isolation and purification can be done by easy and simple procedures such as a common recrystallization without requiring any reduction step. Therefore, it is considered that in the reaction, the iron complex and/or quinone derivative of the compound represented by the general formula (2) are not formed or formations thereof are significantly inhibited. Further, since the production process of the present invention is the one in which most of metals including the metal such as iron used in the reaction can be efficiently removed by a easy and simple procedures such as a usual recrystallization, as obvious from the measurement results of iron ion content in Example 1, it is a superior process which does not require a special step to remove metals (metal oxides) such as iron and the like. In addition, the production process of the present invention has less environmental load because combined use of oxidizing agent such as organic peroxide is not needed, and does not require a complicated step such as reduction, liquid separation, extraction. Therefore, the production process of the present invention is an advantageous process for production in an industrial scale.

Furthermore, from the results of Examples 4 to 7 and Experimental Example 1, the crystal obtained by combining the production process of the present invention and further the specified crystal precipitation process (crystallization method) has a more superior thermal stability compared with the well-known type B crystal. Namely, as obvious from the results of Example 6 and Comparative Example 1, the type B' crystal of 2,3,6,7,10,11-hexahydroxytriphenylene monohydrate obtained in Example 4 has a similar X-ray powder diffraction spectrum to that of the type B crystal of 2,3,6,7,10,11-hexahydroxytriphenylene monohydrate obtained in Comparative Example 1. However, as obvious from the results of Example 7, the type B' crystal does not have thermal decomposition temperature (Td) which is possessed by the known type B crystal, and further, as obvious from the results of Experimental Example 1, the type B' crystal has a superior thermal stability differing from the well-known type B crystal. Therefore, it is suggested that the type B' crystal of 2,3,6,7,10,11-hexahydroxytriphenylene monohydrate according to the present invention is a compound having a different structure from that of the well-known type B crystal. On the other hand, the type C crystal of 2,3,6,7,10,11-hexahydroxytriphenylene monohydrate according to the present invention is a novel crystal which shows a X-ray powder diffraction spectrum and a thermal decomposition temperature (Td) both different from those of the well-known crystal of 2,3,6,7,10,11-hexahydroxytriphenylene monohydrate, and the crystal is superior in thermal stability. Thus, since the type B' crystal and the type C crystal of 2,3,6,7,10,11-hexahydroxytriphenylene monohydrate obtained by combining the production process of the present invention and further the specified crystal precipitation process (crystallization method) are superior in thermal stability, an equipment built-in with the crystal of the present invention as a raw material of a functional material has a superior stability (resistance to denaturalization) and can maintain a desired performance over a long period of time.

INDUSTRIAL APPLICABILITY

The production process of the present invention allows an industrial production and the like of hydroxytriphenylenes which are useful as a raw material of functional materials such as, for example, discotic liquid crystal and the like. In addition, since the novel crystal of 2,3,6,7,10,11-hexahydroxytriphenylene monohydrate of the present invention is superior in thermal stability, for example, when the crystal is used as a raw material of a functional material for equipment, the crystal allows a desired performance of the equipment to be maintained for a long period of time.

What is claimed is:
1. A crystal of 2,3,6,7,10,11-hexahydroxytriphenylene monohydrate obtained by a method comprising:
   reacting catechol in the presence of a metal oxide comprising:
   at least one metal selected from the group consisting of trivalent iron, pentavalent vanadium, and hexavalent molybdenum; and
   a nonvolatile strong acid,
   dissolving resultant 2,3,6,7,10,11-hexahydroxytriphenylene in a mixed solvent of acetone and water, and
   then adding water to an obtained solution at a temperature in a range from 5 to 50° C.
2. A crystal of 2,3,6,7,10,11-hexahydroxytriphenylene monohydrate having, in a X-ray diffraction spectrum for CuKα characteristic X-ray (wavelength: 1.5418 Å), main peaks at 9.3, 10.2 and 26.4 in Bragg angle (2θ±0.2°) thereof, and not having any peak between 10.5 and 12.5.
3. The crystal according to claim 2, wherein a thermal decomposition temperature (Td) is 140° C.

* * * * *